US006353225B1

(12) United States Patent
Strzoda et al.

(10) Patent No.: US 6,353,225 B1
(45) Date of Patent: Mar. 5, 2002

(54) METHOD FOR THE SELECTIVE DETECTION OF GASSES AND GAS SENSOR FOR CARRYING OUT THIS METHOD

(75) Inventors: Rainer Strzoda; Erhard Magori, both of Munich; Maximilian Fleischer, Hoehenkirchen; Hans Meixner, Haar, all of (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/065,336

(22) Filed: Apr. 23, 1998

(30) Foreign Application Priority Data

Apr. 23, 1997 (DE) .......................................... 197 17 145

(51) Int. Cl.[7] .............................................. G01N 21/35
(52) U.S. Cl. ............................ 250/339.13; 250/339.03; 250/339.06; 250/340
(58) Field of Search .......................... 250/340, 339.13, 250/339.12, 339.03, 339.06, 339.07, 343

(56) References Cited

U.S. PATENT DOCUMENTS

| 5,047,639 | A | * | 9/1991 | Wong .......................... 250/341 |
|---|---|---|---|---|
| 5,173,749 | A | * | 12/1992 | Tell et al. .................... 356/437 |
| 5,223,715 | A | * | 6/1993 | Taylor ......................... 250/343 |
| 5,317,156 | A | * | 5/1994 | Cooper et al. .............. 250/345 |
| 5,381,010 | A | * | 1/1995 | Gordon ....................... 250/343 |
| 5,448,071 | A | * | 9/1995 | McCaul et al. ............. 250/343 |
| 5,464,982 | A | * | 11/1995 | Drucker et al. ............. 250/343 |
| 5,502,308 | A | * | 3/1996 | Wong ......................... 250/338.5 |
| 5,506,685 | A | * | 4/1996 | Grasdepot ................... 356/409 |
| 5,625,189 | A |  | 4/1997 | McCaul et al. |
| 5,637,872 | A | * | 6/1997 | Tulip ........................ 250/338.5 |
| 5,705,816 | A | * | 1/1998 | Ronge et al. .............. 250/345 |
| 5,734,165 | A | * | 3/1998 | Unal et al. ................. 250/338.1 |
| 5,748,325 | A | * | 5/1998 | Tulip .......................... 356/437 |
| 5,767,976 | A | * | 6/1998 | Ankerhold et al. ......... 356/437 |

FOREIGN PATENT DOCUMENTS

| EP | 0 709 659 A2 | 5/1996 |
|---|---|---|
| EP | 0 768 523 A2 | 4/1997 |
| GB | 2 231 951 A | 11/1990 |
| JP | 401009341 A | * 1/1989 |

OTHER PUBLICATIONS

Uehara et al, "Real–time monitoring of environmental methane and other gases with semiconductor lasers: a review", *Sensors and Actuators*, B–38–39 (1997). pp. 136–140.
"Electric apparatus for the detection of combustible gases in domestic premesis", *European Standard Final Draft prEN 50194*, May 1995.
Shimose et al, "Remote Sensing of Methane Gas by Differential Absorption Measurement Using a Wavelength Tunable DFB LD", *IEEE Photonics Technology Letters*, vol. 3, No. 1, Jan. 1991, pp. 86–87.
Uehara et al, "Remote detection of methane with a 1.66–$\mu$m diode laser", *Applied Optics*, Feb. 20, 1992, vol. 31, No. 6, pp. 809–814.
Martinelli et al, "Near–Infrared InGaAs/InP Distributed–Feedback Lasers for Spectroscopic Applications", *Proc. Spie–In. Soc.Opt.Eng. (USA), Laser Diode Technology and Applications VI*, vol. 2148, 1994, pp. 292–307.
M.T. Pichery, "Les détecteurs de gaz domestiques par méthode optique", *GAZ d'aujourd'hui*, No. 6, 1996, pp. 271–274.

* cited by examiner

*Primary Examiner*—Constantine Hannaher
(74) *Attorney, Agent, or Firm*—Schiff Hardin & Waite

(57) ABSTRACT

A method an apparatus uses the narrow-band measurement of the absorption of given spectral lines of a gas using laser light sources, so that the spectrally resolved measurement of individual absorption lines, and thus the selection of an individual gas component, is possible. A laser diode which is operated at a higher temperature is correspondingly varied over a certain temperature region, wherein the selected spectral line is crossed. On the basis of absorption measurements, the method and sensor deliver the gas concentration, with a high selectivity.

15 Claims, 2 Drawing Sheets

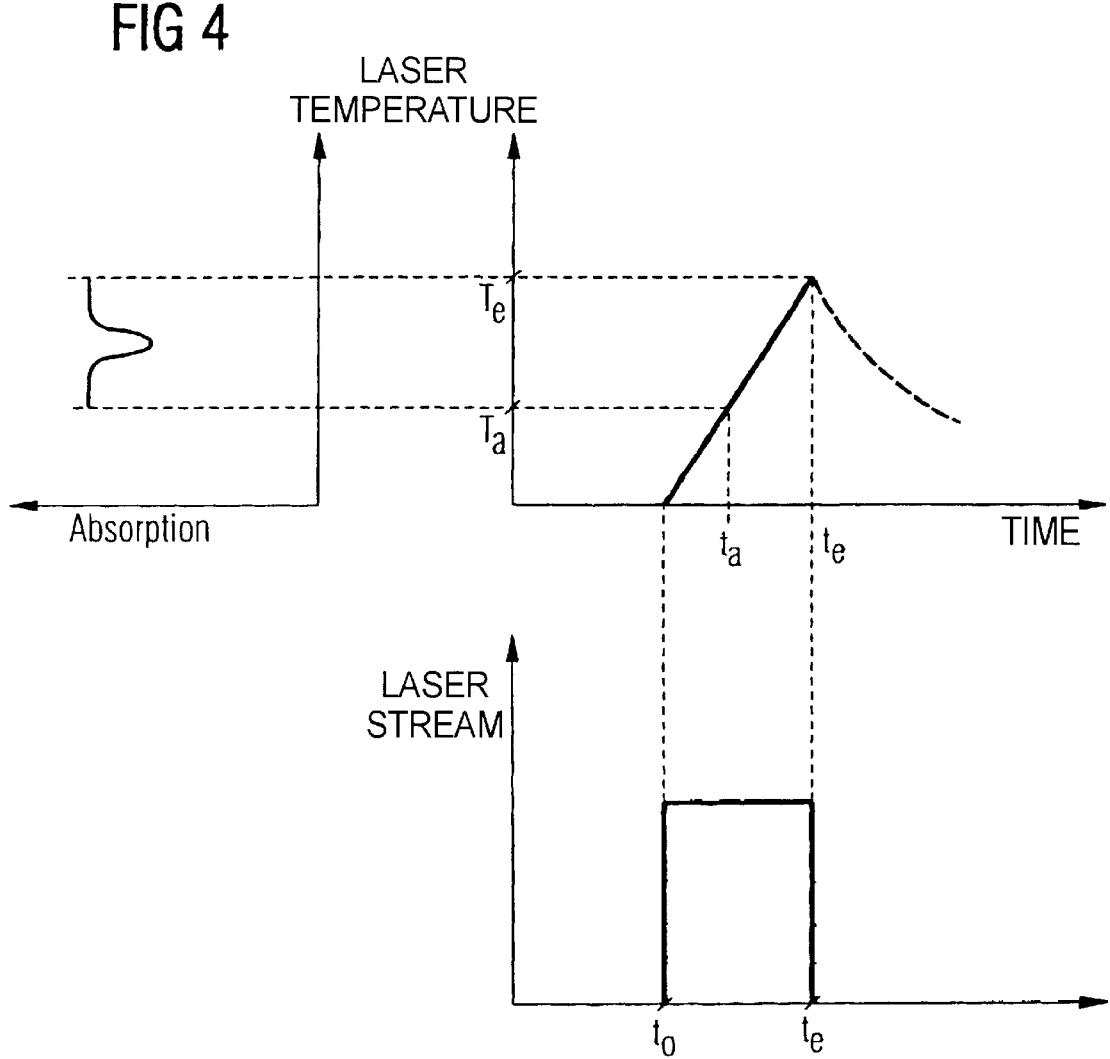

METHOD FOR THE SELECTIVE DETECTION OF GASSES AND GAS SENSOR FOR CARRYING OUT THIS METHOD

FIELD OF THE INVENTION

The invention relates to a method and a gas sensor for selective gas detection, as well as for measuring the corresponding gas concentration through the utilization of light beams in the near infrared region.

BACKGROUND OF THE INVENTION

There is a great need for cost-effective and reliable gas sensors for a number of tasks in the area of safety, comfort and environmental protection. In particular, the air has to be monitored for gas concentrations which are explosive, toxic or uncomfortable to humans. The improved characteristics of the DFB laser diodes (distributed feed back) available today can be advantageously used in optical detection in the near infrared region. The material system InGaAsP (Indium Gallium Arsenid Phosphid) enables the manufacture of laser diodes in the wavelength region between 1.1 and 2.0 $\mu$m. The spectral single-mode DFB laser diodes, which can also meanwhile be manufactured for operating temperatures up to 100° C., are particularly suitable for gas detection. As for the gasses, there exist molecules which comprise absorption bands in the near infrared region. There are, for example, $H_2O$, $CO$, $CO_2$, $NH_3$, HF, $CH_4$, HCL, $NO_2$, $O_2$ which should be mentioned here.

Specific hydrogen-containing molecules such as methane ($CH_4$) show a relatively strong absorption in this wavelength region, which simplifies the technical feasibility of the detection and thus favors the application of laser diodes in the near infrared region for methane detection.

For safety in contact with furnaces driven by natural gas and with stoves in the domestic area, as well as in underground working and the development and supplying of natural gas, there is a need for methane sensors which are in the position to detect with certainty methane concentrations which are far below the ignition threshold (5 Vol %). For this, a detection threshold between 3 and 20% (corresponding to 0.15–1 Vol %) of the lower ignition limit is required. The following norm applies thereto: "Electric apparatus for the detection of combustible gases in domestic premises", Europäische Norm, Final Draft prEN 50194, May 1995. Just as important as the certain detection of the methane is the exclusion of false alarms due to interfering gasses or due to altering events of the sensor. In addition, the freedom from maintenance and long-term stability of the calibration are indispensable for utilization in the private household.

Methane detection is currently carried out with solid-state sensors. Currently available sensors are inadequate for the following reasons. Pellistor gas detectors, which detect on the basis of a catalytic combustion of the methane, are susceptible to certain interfering gasses such as silicon-containing gasses, for example. The interfering gasses effect a sensitivity loss and thus call into question the certainty of detection.

Metal oxide detectors are also utilized for methane detection. The most frequently used material for this is tin oxide. These sensors are generally cross-sensitive to other reducing gasses and also to air moisture, which can lead to false alarms. Reducing gasses are, for example, alcohol, propane/butane as fuel gas for gas cylinders, or volatile organic gasses. However, false alarms result in gas warnings no longer being taken seriously. The combination of a gas detection with an automatic shutoff of the gas supply in the case of an alarm leads to uncertainty and irritation of the user if the gas detection is unreliable and false alarms occur.

The maintenance-free lifetime of the known solid-state sensors lies between one and five years. The lifetime for a methane detector desired by the marketplace, however, is over ten years.

Besides the solid-state sensors, infrared absorption in the hydrocarbon band at 3 $\mu$m wavelengths is also used. The wavelength selection ensues therein with an interference filter. Due to the opposing superposition of the absorption bands of the different hydrocarbons, this method does not permit a selective detection of methane, for example. In the absorption measurement in the near infrared region (NIR) with laser diodes, specific emphases are set. As a rule, the detection method concerns the smallest concentrations, this being connected with costly measurement arrangements. The following literature is cited in this regard: Y.Shimose, T. Okamoto, A. Maruyama, H. Nagai, "Remote sensing of Methane Gas by Differential Absorption Measurement Using a Wavelength Tunable DFB LD, IEEE Photonics Technology Letters", Vol 3, No.1, January 1991, 86–87; Kiyoji Uehara, Hideao Tai, "Remote detection of methane with a 1.66 $\mu$m diode laser", Applied Optics, Feb. 20, 1992, Vol. 31, No. 6, 809–814; and R. U. Martinelli, R. J. Menna, D. E. Cooper, C. B. Carlisle, H. Riris, "Near-infrared InGaAs/InP Distributed-Feedback Lasers for Spectroscopic Applications, Proc. Spie-In. Soc.Opt.Eng. (USA)", Laser Diode Technology and Applications VI, Vol 2148, 292–307, 1994.

A construction for detecting methane with laser diodes in the second harmonic band of methane at 1.325 $\mu$m was proposed by M. T. Pichery, "Les detecteurs de gaz domestiques par methode optique, Gaz d'aujourd'hui", No. 6,1996, 271–273. Due to the low absorption strength in the second harmonic band, a multipath cell with a large absorption distance (larger than 1 m) is therein required. In this construction here described, a cost-effective construction of a sensor of this type remains at the forefront.

The concentration determination of gasses with infrared technology is based on the absorption measurement in the vibration-rotation bands of the gasses. For the optical absorption, the well-known Lambert-Beersche absorption law applies:

$$I(v)=I_0 \cdot e^{-\alpha(v)c \cdot l}$$

Therein, $I_0$ is the irradiated intensity, c is the gas concentration, and $\alpha$ ($\mu$) is the wavelength-dependent absorption coefficient. The absorption takes place inside the optical wavelength l. $\alpha$ ($\mu$) is composed of the line width and absorption profile (Lorenz profile for normal pressure).

SUMMARY OF THE INVENTION

It is the object of the invention to make available a method and a gas sensor for the selective detection of given gasses, wherein the requirements with reference to the detection limits and the reliability are increased, and the sensor construction is cost-effective.

The invention is based on the principle that the narrow-band measurement of the absorption by means of laser light sources enables the spectrally resolved measurement of individual absorption lines and thus the selection of an individual gas component. The harmonics of the molecular vibrations lie in the near infrared region. With the material system InGaAsP, laser diodes which emit light in this region can be manufactured. The region of the near infrared light extends approximately from 0.65 to 2 μm wavelengths. The spectral line width of the laser is less than 10 MHz and thus lies at 0.01 times the half-width value of a typical gas absorption line. The dependency of the emission wavelength of the cited laser diodes on the temperature (typically 0.1 nm/K), or respectively, on the laser stream or flux is used to pick up the spectrum of at least one absorption line. If two spectral lines lie relatively close together, then it can make sense to pick up more than one line. The spectrum can be compared to a theoretical calculation of the absorption line, wherein, as significant parameter, the gas concentration is obtained from the comparison. This method comprises two significant advantages. For one, a calibration of the measurement construction with test gasses is omitted. Secondly, this method is to a great extent independent of the transmission of the absorption distance (measured length), so that contaminations of optical windows have no effect on the measurement result.

Accordingly, the present invention provides a method for selectively detecting and measuring the concentration of a gas through light absorption in the near infrared region. The method includes the steps of selecting at least one spectral line of the spectrum of the gas to be detected and selecting a distributed feed back laser diode with an emission wavelength in the near infrared region that is dependent upon an operating temperature of the laser diode and that corresponds to the selected spectral line. The method further includes the steps of maintaining the laser diode at a temperature that is greater than or equal to 40° C. and emitting light from the laser diode having an emission wavelength in the near infrared region. The light is emitted across a measured distance to a photodetector. Thereafter, the gas is detected by varying the operating temperature of the laser diode so that the emission wavelength of the light emitted from the laser diode overlaps the spectral line of the gas to be detected. The concentration of the gas is measured by measuring an absorption difference at the photodetector in a wavelength region that corresponds to the selected spectral line at two different operating temperatures of the laser diode and thereafter calculating the concentration of the gas to be measured from the absorption difference.

In an embodiment, the operating temperature of the laser diode is varied by utilizing an electrical resistance heating element which heats the laser diode.

In an embodiment, the operating temperature of the laser diode is varied by emitting light from the laser diode which heats the laser diode.

In an embodiment, the method further includes the step of callibrating the photodetector by measuring an absorption of a known reference gas of a known concentration and composition.

In an embodiment, the reference gas is disposed in a hollow enclosure directly in front of the laser diode so that light emitted from the laser diode passes through the reference gas before it reaches the photodetector.

In an embodiment, the reference gas comprises a known concentration of the gas to be measured and detected.

In an embodiment, the present invention provides a gas sensor which comprises a housing having two opposing ends with a laser diode and photodetector disposed at one opposing end and a hollow mirror disposed at an opposing end. Light emitted from the laser diode is reflected off of the hollow mirror and back to the photodetector. The middle portion of the housing has a defined distance and is filled with a gas to be measured.

In an embodiment, the housing further comprises a hollow enclosure filled with a reference gas. The hollow enclosure is disposed in front of the laser diode so that light emitted from the laser diode passes through the reference gas before it reaches the hollow mirror.

Other objects and advantages of the invention will become apparent upon reading the following detailed description and appended claims, and upon reference to the accompanying drawings.

BRIEF DESCRIPTION OF THE DRAWINGS

Exemplifying embodiments are described using the accompanying schematic figures, wherein:

FIG. 4 illustrates, graphically, the temperature determination of the laser wavelength with a current pulse of constant amplitude.

Figure 1:
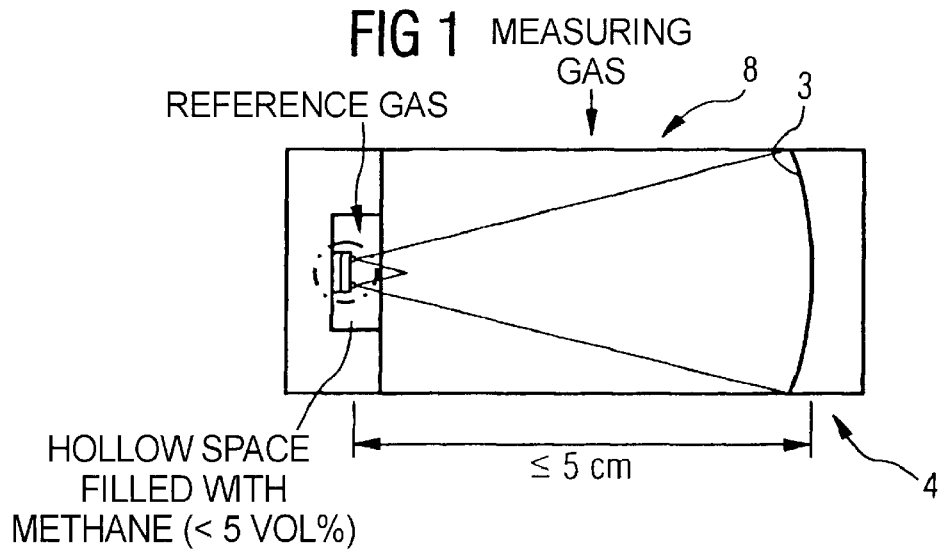
FIG. 1 illustrates, schematically, a compact construction of a methane detector with laser diode, hollow mirror and photodetector.
Figure 2:
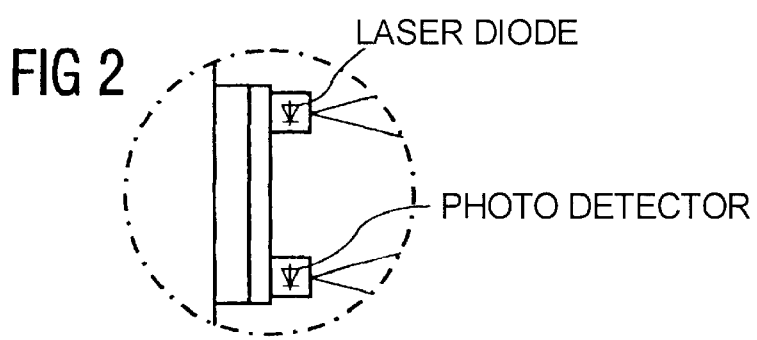
FIG. 2 illustrates an enlarged excerpt from FIG. 1.

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

DETAILED DESCRIPTION OF THE PRESENTLY PREFERRED EMBODIMENT

Laser diodes generally comprise a strongly divergent emission characteristic (aperture angle 10° to 40°). When the measurement ensues in the first harmonic band at 1.66 μm, for measuring the smallest required methane concentration (e.g. 1500 ppm), the methane detector described here must have an absorption distance (measured length) of less than 10 cm. The compact detector construction results from the utilization of a single hollow or concave mirror 3 (see FIG. 1) which traps the divergent laser light and focuses this on the photodetector 2. The beam path is therein conducted through the measurement gas 6 twice.

The following advantages arise through this construction: First, through the folding of the absorption path, the structural length is halved to a first approximation; second relative to the conventional construction, an optical element is omitted, such as a lens; and third, the laser 1 and photodetector 2 can be accommodated in a common housing 4, making the manufacture of the sensor easier and less expensive.

The laser exit window is advantageously not imaged in a 1:1 ratio on the photodetector 2, but rather enlarged, such that only a part of the beam reaches the photodetector 2. The following advantages emerge therefrom: First, the justifying of the concave mirror is simplified; second, a dejustifying of the optic during the operation does not lead to a loss of the signal; and third, photodiodes with small faces can be used, wherein the operation in the linear region of the characteristic is guaranteed, so that overdrives are avoided.

Figure 3A:
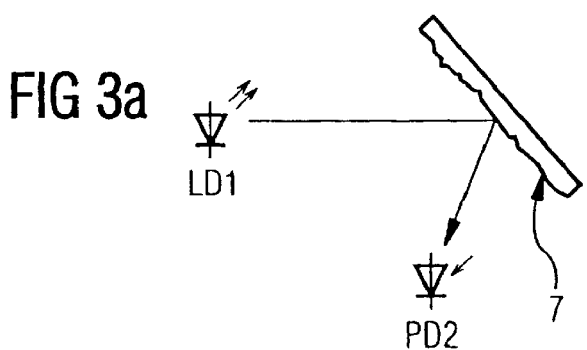
FIGS. 3a and 3b illustrate, schematically, a methane detector without focusing optical elements, with folded and with extended construction.
Figure 3B:
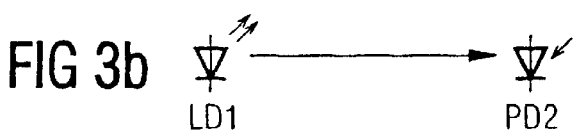

Instead of the concave mirror 3 as shown in FIG. 1, a diffusely reflective surface can also be utilized. The photodetector 2 must therein be attached in such a way that a portion of the reflected light strikes at its surface, as depicted in FIG. 3a. Instead of the folded construction according to FIG. 3a, an extended construction without optical elements can be utilized (see FIG. 3b). Significant advantages can be achieved, however, with the construction according to FIG. 1 using a concave mirror 3.

In a measurement system using laser diodes, the laser radiation is often split into a measurement branch and a reference branch. In the reference branch, a gas, or respectively, a gas cell is located which has a sufficient concentration of the gas component to be measured. The absorption in the reference cells is used to stabilize the wavelength of the laser diode 1 at the gas absorption line.

The wavelength dependency of the laser emission on the temperature would first require the checking of the laser temperature, in order to set a predetermined light wavelength. To this end, the laser is generally run on a heat sink with a Peltier element. A temperature probe is used to hold the temperature at a constant level. The new DFB laser diodes permit an operation above the normal environmental temperature. The temperature stabilization of the laser diode 1 can thus ensue with an electrical resistance heating instead of a Peltier element. This heating can be realized directly on the laser chip, or respectively, on its carrier. The temperature measurement ensues preferably with a metal-film resistor which is placed onto the surface of the laser chip. The temperature dependency of the laser diode characteristic can be used just as well for the temperature measurement.

In the inventive methane detector, a reference gas cell is arranged directly in the measurement branch, so that a permanent preabsorption takes place. The preabsorption is applied in the measurement system for relative wavelength calibration. The gas concentration to be measured is obtained from the growth of the absorption. It is to be noted therein that the reference cells can be constructed as independent optical cells. It is, however, advantageous to design the housing 4 such that a reference gas cell with the corresponding reference gas 5 is integrated in the housing.

According to FIG. 1, a hollow space is provided in which a reference gas with methane is contained, so that a wavelength calibration is possible. The absorption, which is thereby constantly present on the basis of the presence of methane, must be considered in the total absorption. Alternatively to the reference gas 5 which contains a portion of the gas to be detected (measurement gas 6), a neighboring atmospheric absorption line of $H_2O$ or $CO_2$, for example, can be applied for wavelength absorption.

FIGS. 1, 2 and 3a and 3b depict details of gas sensors such as the laser diode 1, the photodetector 2, the hollow mirror 3, the housing 4, a reference gas 5, a measurement gas 6, a measured length 8, and a diffusely reflective surface 7. According to FIG. 1, an inventive gas sensor comprises a very low structural size by reason of the folding of the beam path through the measurement gas 6. The hollow mirror 3 provides for corresponding focusing of the beam paths. The reference gas 5 is accommodated in a reference gas cell inegrated in the housing 4, and this reference gas surrounds the laser diode 1 and the photodetector 2.

The method, or respectively, the varying of the laser diode temperature is described FIG. 4. The varying of the laser diode temperature for spectral measurement can occur in different ways. The wavelength dependency of the laser diode 1 on the laser diode operating temperature is inventively exploited. This temperature is effected either through an external heating with a corresponding controlling or through the laser stream itself. In the described methane detector, the varying temperature ensues through the application of a constant stream at a time $t_0$ at the laser diode according to FIG. 4. Conditional to the energy dissipation in the track resistance of the real diode, the laser heats up. The speed of the temperature change is therein dependent on the supplied power, the heat capacity of the chip and the heat transmission resistance to the environment. The spectral measurement is performed during the temperature rise. If the laser chip temperature is simultaneously measured, then an external temperature controlling is superfluous. The measurement is then initiated with the achievement of the start temperature $T_a$ (which corresponds to a certain light wavelength) and ended with the achievement of the stop temperature $T_e$. If an adaptive system is present, then a constantly accompanying temperature measurement can be forgone, since, for example, the laser diode with the stream is varied over the maximal temperature region. The corresponding measurement region with the limits of the start time $t_a$ and the stop time $t_e$ can be defined using the measured reference absorption and the known characteristic field of the laser diode. The absorption line then lies in the measurement window. A deviation from the ideal situation of the absorption as a result of a change of the environmental temperature can be continually corrected from one measurement to the next through adjustment of the start, or respectively, stop times.

The three related diagrams of FIG. 4 show that the laser diode 1 is operated with a constant stream within the time limits $t_0$ and $t_e$. The measurement time lies within the time limits $t_a$ and $t_e$. A measurement lasts one second, for example, and is repeated every 30 seconds. Because of the temperature dependence of the emission wavelength of the laser, the laser temperature rises from Ta to Te within the time window $t_a-t_e$. This region for the varying of the laser temperature is inventively applied to one or more selected spectral lines of the gas to be measured. It is thus assured that, in the present measurement of gas 6, the spectral line is detectable—or respectively, in the use of an identical reference gas, an absorption difference in the form of a reduction in intensity of the received light is detectable. Because the spectral line width of the laser is 100 times lower than the half-width value for a typical gas absorption line (spectral line), the selected spectral line can be very exactly sensed, or respectively, scanned. The laser diode 1 is therein operated above room temperature, so that it can cool again from the stop temperature $T_e$ until the next measurement cycle. A minimal distance of the start temperature $T_a$ to room temperature is thus necessary. An upper room temperature limit consists of the maximal operating temperature of a laser diode 1 above which no more light emission takes place. Since further developments in laser diodes take place regularly, it is merely pointed out that laser diodes with a maximal operating temperature of more than 100° C. are currently available. Since in the inventive method, or respectively, with the corresponding gas sensor gas concentrations occur on the basis of the absorption, measurement, then, in addition to the described function, the function of a smoke alarm can also be taken over, if an excessive decrease of the total transmission arises within a short time. To this end, the rapid change of the total transmission of the absorption distance is evaluated.

The method can be performed well by reason of the properties of methane. The detection of other gases in the near infrared region can be performed just as well, however.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

What is claimed is:

1. A method for selectively detecting and measuring the concentration of a gas through light absorption in the near infrared region, the gas emitting a spectrum with a plurality of spectral lines upon being exposed to light in the near infrared region, the method comprising the following steps:

selecting at least one spectral line of the spectrum of the gas to be detected, selecting a distributed feed back laser diode with a range of emission wavelengths in the near infrared region that is dependent upon an operating temperature of the laser diode greater than or equal to 40° C. and that encompasses the selected spectral line, emitting light having an emission wavelength in the near infrared region from the laser diode across a measuring distance to a photodetector, detecting the gas by monotonically increasing the operating temperature of the laser diode in a range starting at least at 40° C. so that the emission wavelength of the light emitted from the laser diode monotonically increasingly sweeps said range of emission wavelengths thereby insuring coverage of the spectral line of the gas to be detected, and measuring the concentration of the gas by measuring an absorption difference at the photodetector in a wavelength region corresponding to the selected spectral line at two different operating temperatures of the laser diode in said sweep and calculating the concentration of the gas to be measured from the absorption difference.

2. The method of claim 1 wherein the step of detecting the gas by varying the operating temperature of the laser diode is carried out with an electrical resistance heating element which heats the laser diode and which is located on the laser diode.

3. The method of claim 1 wherein the laser diode is mounted on a carrier and the step of detecting the gas by varying the operating temperature of the laser diode is carried out with an electrical resistance heating element which heats the laser diode and which is located on the carrier.

4. The method of claim 1 wherein the step of detecting the gas by varying the operating temperature of the laser diode is carried out by emitting light from the laser diode which results in a heating of the laser diode.

5. The method of claim 1 further comprising the step of calibrating the photodetector by measuring an absorption of a known reference gas of a known composition and concentration.

6. The method of claim 5 wherein the reference gas is located in a concave enclosure directly in front of the laser diode and along the measuring distance.

7. The method of claim 5 wherein the reference gas comprises the gas to be detected and measured.

8. The method of claim 5 wherein the reference gas is free of the gas to be detected and measured and has a spectral line that is different than the selected spectral line of the gas to be detected and measured.

9. The method of claim 1 wherein the gas to be detected and measured is methane and the selected spectral line has a wavelength of 1.65 $\mu$m.

10. The method of claim 1 further comprising the step of sounding an alarm in the event a substantial decrease in the absorption at the photodetector is detected.

11. A method for selectively detecting the concentration of a gas through light absorption in the near infrared region, the gas emitting a spectrum with a plurality of spectral lines upon being exposed to light in the near infrared region, the method comprising the following steps:

selecting at least one spectral line of the spectrum of the gas to be detected, selecting a distributed feed back laser diode with a range of emission wavelengths in the near infrared region that is dependent upon an operating temperature of the laser diode and that encompasses the selected spectral line, operating the laser diode in a range of monotonically increasing temperature starting at least at 40° C. to produce light in a monotonically increasing range off emission wavelengths in the near infrared region and directing the light across a measurement distance to a photodetector, and detecting the gas as the operating temperature of the laser diode increases so that the emission wavelength of the light emitted from the laser diode is insured to cover the spectral line of the gas to be detected.

12. The method of claim 11 further comprising the steps of measuring the concentration of the gas by measuring an absorption difference at the photodetector in a wavelength region corresponding to the selected spectral line at two different operating temperatures of the laser diode, and calculating the concentration of the gas to be measured from the absorption difference.

13. The method of claim 11 further comprising the step of calibrating the photodetector by measuring an absorption of a known reference gas of a known composition and concentration.

14. The method of claim 13 wherein the reference gas is located in a hollow space directly in front of the laser diode and along the measurement distance.

15. A method for selectively detecting the concentration of a gas through light absorption in the near infrared region, the gas emitting a spectrum with a plurality of spectral lines upon being exposed to light in the near infrared region, the method comprising the following stepsselecting selecting at least one spectral line of the spectrum of the gas to be detected, selecting a distributed feed back laser diode with a range of emission wavelengths in the near infrared region that is dependent upon an operating temperature of the laser and that encompasses the selected spectral line, operating the laser diode in a monotonically increasing range of temperature greater than or equal to 40° C. to produce light at monotonically increasing wavelengths in a range of emission wavelengths in the near infrared region, which overlaps the spectral line of the gas to be detected;

calibrating the photodetector by measuring an absorption of a known reference gas of a known composition and concentration, the reference gas being located in a concave enclosure directly in front of the laser diode;

directing the light across a measuring distance containing a sample to a photodetector, detecting the gas as the operating temperature of the laser diode is monotonically increased so that the emission wavelength of the light emitted from the laser diode is insured to overlap the spectral line of the gas to be detected, measuring the concentration of the gas by measuring an absorption difference at the photodetector in a wavelength region corresponding to the selected spectral line at two different operating temperatures of the laser diode, and calculating the concentration of the gas to be measured from the absorption difference.

* * * * *